United States Patent
Kawai et al.

(10) Patent No.: US 11,424,145 B2
(45) Date of Patent: Aug. 23, 2022

(54) TRANSFER CHAMBER

(71) Applicant: SINFONIA TECHNOLOGY CO., LTD., Tokyo (JP)

(72) Inventors: Toshihiro Kawai, Tokyo (JP); Takashi Shigeta, Tokyo (JP); Munekazu Komiya, Tokyo (JP); Yasushi Taniyama, Tokyo (JP)

(73) Assignee: SINFONIA TECHNOLOGY CO., LTD., Minato-ku (JP)

( * ) Notice: Subject to any disclaimer, the term of this patent is extended or adjusted under 35 U.S.C. 154(b) by 0 days.

(21) Appl. No.: 16/845,555

(22) Filed: Apr. 10, 2020

(65) Prior Publication Data
US 2020/0312686 A1   Oct. 1, 2020

Related U.S. Application Data

(62) Division of application No. 15/554,135, filed as application No. PCT/JP2016/053553 on Feb. 5, 2016, now Pat. No. 10,672,632.

(51) Int. Cl.
*H01L 21/67* (2006.01)
*F24F 13/28* (2006.01)
(Continued)

(52) U.S. Cl.
CPC ........ *H01L 21/67196* (2013.01); *B01D 53/04* (2013.01); *B01D 53/40* (2013.01);
(Continued)

(58) Field of Classification Search
None
See application file for complete search history.

(56) References Cited

U.S. PATENT DOCUMENTS 4,911,597 A   3/1990   Maydan et al.
4,923,352 A * 5/1990   Tamura ............... B25J 21/005
                                                  29/722
(Continued)

FOREIGN PATENT DOCUMENTS

JP    H05-226454 A    9/1993
JP    9-38449 A       2/1997
(Continued)

OTHER PUBLICATIONS

International Search Report dated Apr. 26, 2016, issued in counterpart International Application No. PCT/JP2016/053553 (1 page).
(Continued)

*Primary Examiner* — Ronald P Jarrett
(74) *Attorney, Agent, or Firm* — WHDA, LLP

(57) ABSTRACT

To provide a transfer chamber capable of replacing a chemical filter without affecting an internal atmosphere, and shortening or eliminating stop time of a transfer process of a wafer (W) associated with replacement of the chemical filter.

The transfer chamber transfers the wafer (W) to or from a processing device (6) by using a transfer robot (2) provided thereinside, and includes a circulation path (CL1) formed inside of a transfer chamber (1) to circulate gas, a chemical filter unit (7) provided in the midstream of the circulation path (CL1), and a connecting and disconnecting means (8) which switches connection and disconnection of the chemical filter unit (7) to and from the circulation path (CL1).

20 Claims, 9 Drawing Sheets

(51) Int. Cl.
- *F24F 7/06* (2006.01)
- *B01D 53/04* (2006.01)
- *F24F 7/00* (2021.01)
- *B65G 49/07* (2006.01)
- *H01L 21/677* (2006.01)
- *F24F 3/167* (2021.01)
- *F24F 7/08* (2006.01)
- *H01L 21/673* (2006.01)
- *B01D 53/40* (2006.01)
- *B01D 53/42* (2006.01)
- *C12M 1/12* (2006.01)
- *F24F 6/00* (2006.01)
- *H01L 21/687* (2006.01)

(52) U.S. Cl.
CPC ............. *B01D 53/42* (2013.01); *B65G 49/07* (2013.01); *C12M 37/00* (2013.01); *F24F 3/167* (2021.01); *F24F 6/00* (2013.01); *F24F 7/00* (2013.01); *F24F 7/06* (2013.01); *F24F 7/065* (2013.01); *F24F 7/08* (2013.01); *F24F 13/28* (2013.01); *H01L 21/67017* (2013.01); *H01L 21/67389* (2013.01); *H01L 21/67393* (2013.01); *H01L 21/67766* (2013.01); *H01L 21/68707* (2013.01); *B01D 2258/02* (2013.01)

(56) References Cited

U.S. PATENT DOCUMENTS

| | | | |
|---|---|---|---|
| 5,303,482 A * | 4/1994 | Yamashita | H01L 21/67769 34/218 |
| 5,565,034 A * | 10/1996 | Nanbu | H01L 21/67173 118/668 |
| 5,922,095 A * | 7/1999 | Hustvedt | B01D 45/06 55/385.1 |
| 5,928,390 A * | 7/1999 | Yaegashi | H01L 21/67742 29/25.01 |
| 6,224,679 B1 * | 5/2001 | Sasaki | B08B 5/00 118/719 |
| 8,851,008 B2 * | 10/2014 | Fukutomi | H01L 21/6715 118/64 |
| 2002/0124906 A1 * | 9/2002 | Suzuki | H01L 21/67379 141/98 |
| 2003/0031537 A1 | 2/2003 | Tokunaga | |
| 2004/0144316 A1 * | 7/2004 | Lee | H01L 21/67167 118/719 |
| 2004/0168742 A1 * | 9/2004 | Kim | H01L 21/67017 141/98 |
| 2009/0317214 A1 | 12/2009 | Hsiao et al. | |
| 2014/0273489 A1 * | 9/2014 | Wang | H01L 21/6708 438/716 |
| 2015/0170945 A1 | 6/2015 | Segawa et al. | |

FOREIGN PATENT DOCUMENTS

| | | |
|---|---|---|
| JP | 2003-314873 A | 11/2003 |
| JP | 4550101 B2 | 9/2010 |
| JP | 2012-49382 A | 3/2012 |
| JP | 2014-112631 A | 6/2014 |

OTHER PUBLICATIONS

Extended European Search Report dated Sep. 21, 2018, issued in counterpart application No. 16755180.3. (8 pages).

Non Final Office Action dated Jun. 26, 2018, issued in U.S. Appl. No. 15/554,135.

Non Final Office Action dated Jan. 10, 2019, issued in U.S. Appl. No. 15/554,135.

Final Office Action dated Jul. 19, 2019, issued in U.S. Appl. No. 15/554,135.

* cited by examiner

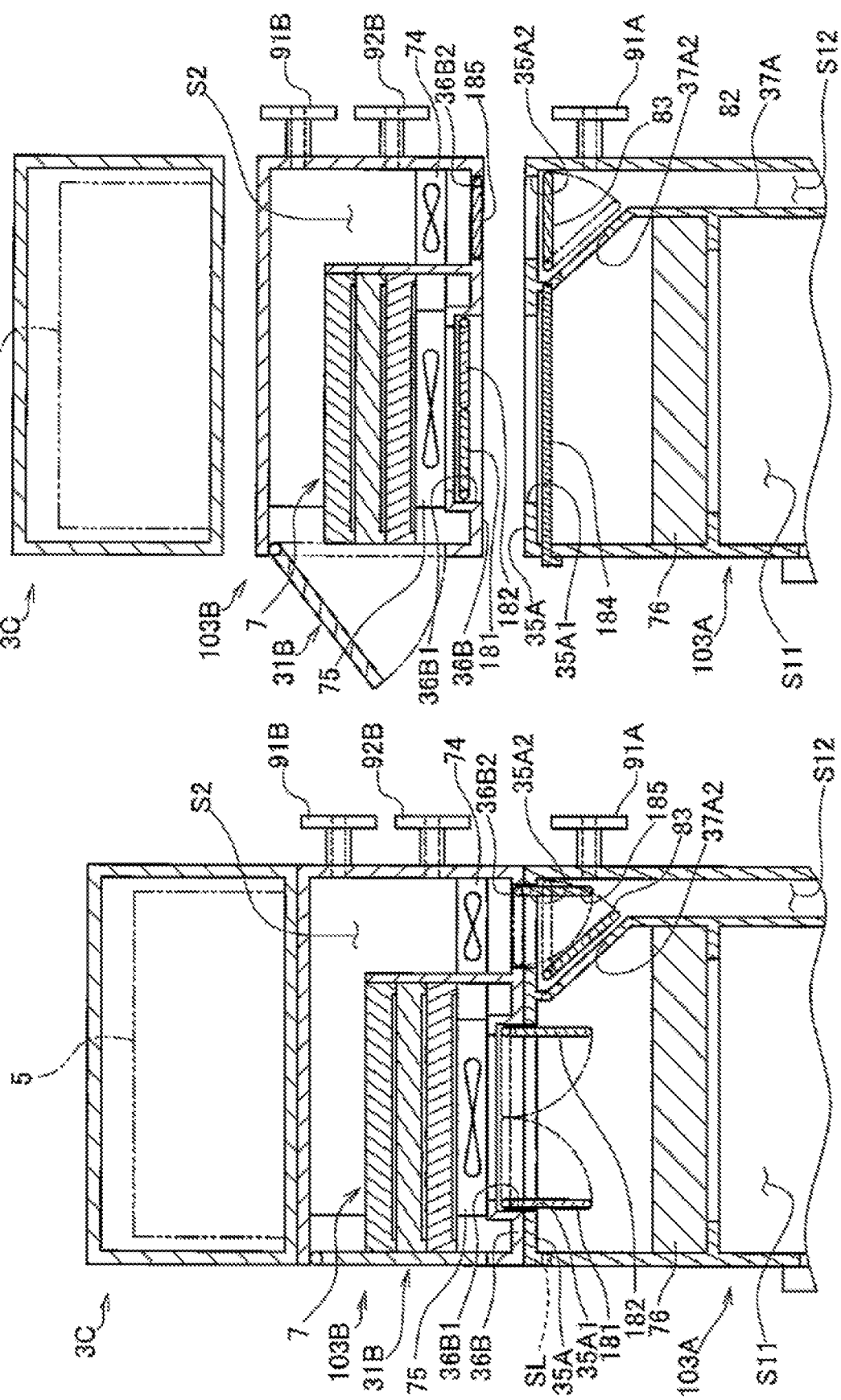

TRANSFER CHAMBER

CROSS-REFERENCE TO RELATED APPLICATIONS

This application is a divisional of U.S. application Ser. No. 15/554,135, filed on Aug. 28, 2017, which is a 371 of International Application No. PCT/JP2016/053553, filed on Feb. 5, 2016, which is based upon and claims the benefit of priority from the prior Japanese Patent Application No. 2015-038388, filed on Feb. 27, 2015, the entire contents of which are incorporated herein by reference.

TECHNICAL FIELD

The present invention relates to a transfer chamber capable of transferring a transferred object in a clean state without exposing to the outside air.

BACKGROUND ART

In the field of semiconductor, a semiconductor device is conventionally manufactured by applying various processing steps to a wafer.

In the semiconductor device manufacturing process, a particle-less and chemical component-less transfer environment of a wafer has been required, and a closed type container called an FOUP (Front-Opening Unified Pod) and a transfer chamber generally called an EFEM (Equipment Front End Module) which transfers a wafer to or from a processing device are used (see the following Patent Literature 1). In the transfer chamber, usually, fresh outside air in a clean room is taken into an FFU (Fun Filter Unit) installed in an upper part, and the air is made to flow downward inside of the transfer chamber and exhausted to the outside from a floor surface, so as to stably obtain a constant clean atmosphere.

Further, as the semiconductor device structure decreases in size recently, influences caused by the moisture content, oxygen, chemical components, and so forth affecting the semiconductor device structure are becoming a more serious problem. To address this problem, replacing the inside of the transfer chamber with N2 (nitrogen) gas which is inactive gas, and transferring a wafer under an N2 atmosphere have been proposed. In that case, in order to reduce consumption of N2 gas and to suppress running cost, since it is necessary to keep the inside clean while reducing the supply amount of fresh N2 gas, it is possible to make N2 gas circulate while passing through a filter.

Further, it is possible to provide a chemical filter to efficiently remove chemical components from the circulating N2 gas. Since chemical components can be carried into the transfer chamber with a wafer which is subjected to a process treatment by the processing device, it is possible to efficiently remove such chemical components by using a chemical filter as a gas processing device and keep a further cleaner atmosphere.

The same technique as described above is used also in the field related to the cell culture as described in the following Patent Literature 2. Inside of the transfer chamber in this case is kept clean by sterilization processing and so forth, and the transfer chamber is configured to transfer a culture vessel, such as a petri dish, to or from an adjacent culture apparatus as a processing device by using a transfer robot provided thereinside. Also in the transfer chamber in the field related to the cell culture, it is possible to obtain a cleaner atmosphere by removing chemical components by using a chemical filter while keeping the atmosphere clean by circulating internal gas through a filter.

CITATION LIST

Patent Literature

Patent Literature 1: JP-A-2012-49382
Patent Literature 2: Japanese Patent No. 4550101

SUMMARY OF THE INVENTION

Problems to be Solved by the Invention

If the gas is made to circulate inside of a transfer chamber as described above, since it is almost unachievable to exhaust chemical components carried in from the processing device to the outside, it is necessary to more efficiently remove the chemical components by using a chemical filter.

Then, replacing the chemical filter at proper timing so that removal efficiency of the chemical component is not impaired becomes more important.

However, since it is necessary to open the entire transfer chamber when replacing the chemical filter, it is necessary to stop the transfer process of the transferred object inside of the transfer chamber. Further, since the atmosphere inside of the transfer chamber in which external gas, such as air, has entered is replaced by replacing the chemical filter, stop time until the transfer process is resumed becomes long, and consumption of the gas increases which causes an increase in cost. During replacement of the chemical filter, particles, and so forth may enter the transfer chamber. In that case, time for making the inside of the transfer chamber clean again is required.

In a transfer chamber used in the field related to the cell culture, a detoxication apparatus as a gas processing device which detoxicates the gas after performing sterilization by the gas may be provided. In that case, the same problem may arise during replacement of such a detoxication apparatus.

An object of the present invention is to effectively solve these issues, and more particularly, to provide a transfer chamber capable of replacing a gas processing device without affecting an internal atmosphere, and shortening or eliminating stop time of a transfer process of a transferred object associated with the replacement of the gas processing device.

Means for Solving the Problem

The following means are provided to solve the above-described problems.

A transfer chamber of the present invention is a transfer chamber for transferring a transferred object to or from a processing device by using a transfer robot disposed thereinside, including: a circulation path formed inside of the transfer chamber to circulate gas; a gas processing device provided in the midstream of the circulation path; and a connecting and disconnecting means configured to switch connection and disconnection of the gas processing device to and from the circulation path.

With this configuration, the gas processing device can be replaced without affecting an internal atmosphere by disconnecting the gas processing device from the circulation path by using the connecting and disconnecting means, so that the inside of the transfer chamber can be kept clean. Further, since it becomes unnecessary to expose the entire inside of the transfer chamber to the outside air during replacement of the gas processing device, it is possible to eliminate or shorten the time for adjusting the atmosphere after the gas processing device is reconnected to the circulation path. Therefore, it becomes possible to eliminate or shorten the stop time of the transfer process of the transferred object associated with the replacement of the gas processing device.

In order to keep the inside clean also when disconnecting the gas processing device by using the connecting and disconnecting means, it is desirable that when the gas processing device is disconnected from the circulation path by the connecting and disconnecting means, a shortened circulation path through which gas circulates without passing through the gas processing device is formed.

In order to enable to perform connection and disconnection of the gas processing device to and from the circulation path, it is desirable that the connecting and disconnecting means is constituted by openable lids which open and close a gas inflow port through which gas flows into the gas processing device and a gas outflow port through which gas flows out of the gas processing device.

In order to improve working efficiency of replacement of the gas processing device and enable to select whether the gas processing device is necessary depending on the type of the transferred object or the contents of the process performed by the processing device, it is desirable that the transfer chamber includes a transfer chamber main body in which the transfer robot is provided, and a gas processing box which contains the gas processing device, wherein the gas processing box is connectable to and disconnectable from the transfer chamber main body, and when connected, the circulation path is formed between the gas processing box and the transfer chamber main body.

In order to properly adjust the atmosphere near the gas processing device before connecting to the circulation path by using the connecting and disconnecting means and not to affect the internal atmosphere even if the transfer chamber is exposed to the outside air during replacement of the gas processing device, the transfer chamber desirably includes a gas purge means configured to replace an atmosphere in the gas processing box which contains the gas processing device when the gas processing device is disconnected from the circulation path by the connecting and disconnecting means.

Further, in order to enable to connect the gas processing device to the circulation path after providing sufficient removal ability even after the replacement of the gas processing device, it is desirable that the gas processing device is a chemical filter, and the transfer chamber includes a moisture supply means which causes moisture content to be contained in the gas supplied to the gas processing box, and a control means which controls the moisture supply means depending on humidity in the gas processing box.

Effect of the Invention

According to the present invention described above, it is possible to provide a transfer chamber capable of replacing a gas processing device without affecting an internal atmosphere, and shortening or eliminating stop time of a transfer process of a transferred object associated with the replacement of the gas processing device.

BRIEF DESCRIPTION OF THE DRAWINGS

FIG. 9A and FIG. 9B are an explanatory view illustrating a modification of the transfer chamber.

MODE FOR CARRYING OUT THE INVENTION

Hereinafter, an embodiment of the present invention will be described with reference to the drawings.

Figure 1:
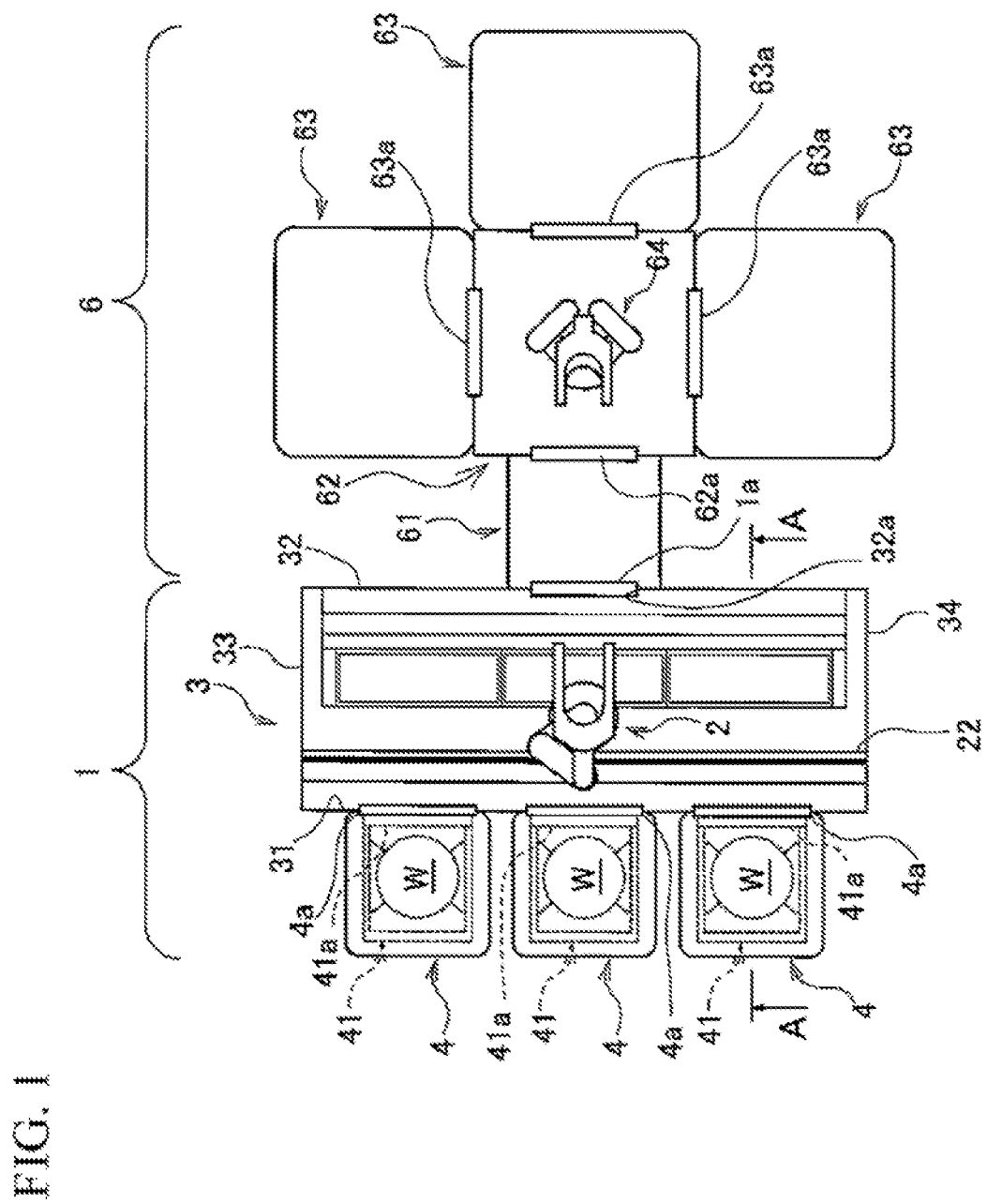
FIG. 1 is a plan view schematically illustrating a relationship between a transfer chamber and a processing device according to an embodiment of the present invention.

FIG. 1 is a plan view schematically illustrating a relationship between a transfer chamber 1 according to an embodiment of the present invention and a processing device 6 connected to the transfer chamber 1. As illustrated in FIG. 1, the transfer chamber 1 is constituted as module equipment generally referred to as an EFEM. In particular, the transfer chamber 1 includes a transfer robot 2 which transfers a wafer W which is a transferred object between prescribed transfer positions, a box-shaped housing 3 provided to surround the transfer robot 2, and a plurality of (three in FIG. 1) load ports 4 connected to the outside of a wall on the front side of the housing 3 (a front wall 31).

Here, in the present application, the direction in which the load ports 4 are connected when seen from the housing 3 is defined as the front side, the direction of a rear wall 32 opposite to the front wall 31 is defined as the rear side, and the directions orthogonally cross the front and rear directions and the vertical direction are defined as side directions. That is, the three load ports 4 are disposed along the side direction.

As illustrated in FIG. 1, a load lock chamber 61 which constitutes a part of the processing device 6 can be connected adjacent to an outside of the rear wall 32 of the transfer chamber 1, and when a door 1a provided between the transfer chamber 1 and the load lock chamber 61 is opened, inside of the transfer chamber 1 and the load lock chamber 61 can communicate with each other. Although various types of devices may be used as the processing device 6, generally, a configuration in which a relay chamber 62 is provided adjacent to the load lock chamber 61, and a plurality of (three in FIG. 1) processing units 63 which perform processing to the wafers W are provided adjacent to the relay chamber 62 is employed. A door 62a is provided between the relay chamber 62 and the load lock chamber 61, and doors 63a are provided between the relay chamber 62 and each of the processing units 63. When the doors 62a and 63a are opened, the load lock chamber 61 and the processing units 63 can communicate with each other, and the wafer W can be moved between the load lock chamber 61 and the processing units 63 by using the transfer robot 64 provided in the relay chamber 62.

Figure 2:
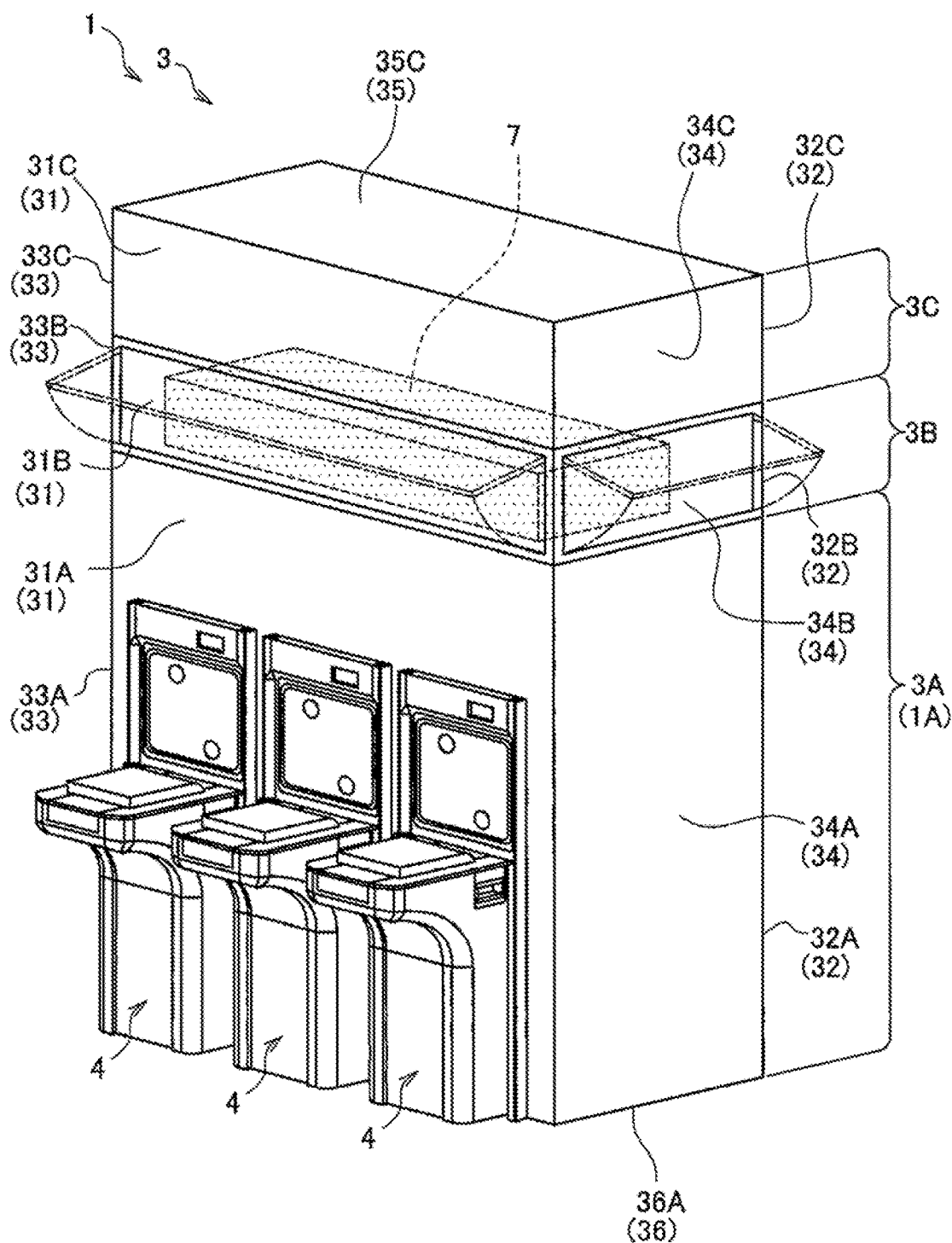
FIG. 2 is a perspective view schematically illustrating the transfer chamber.
Figure 3:
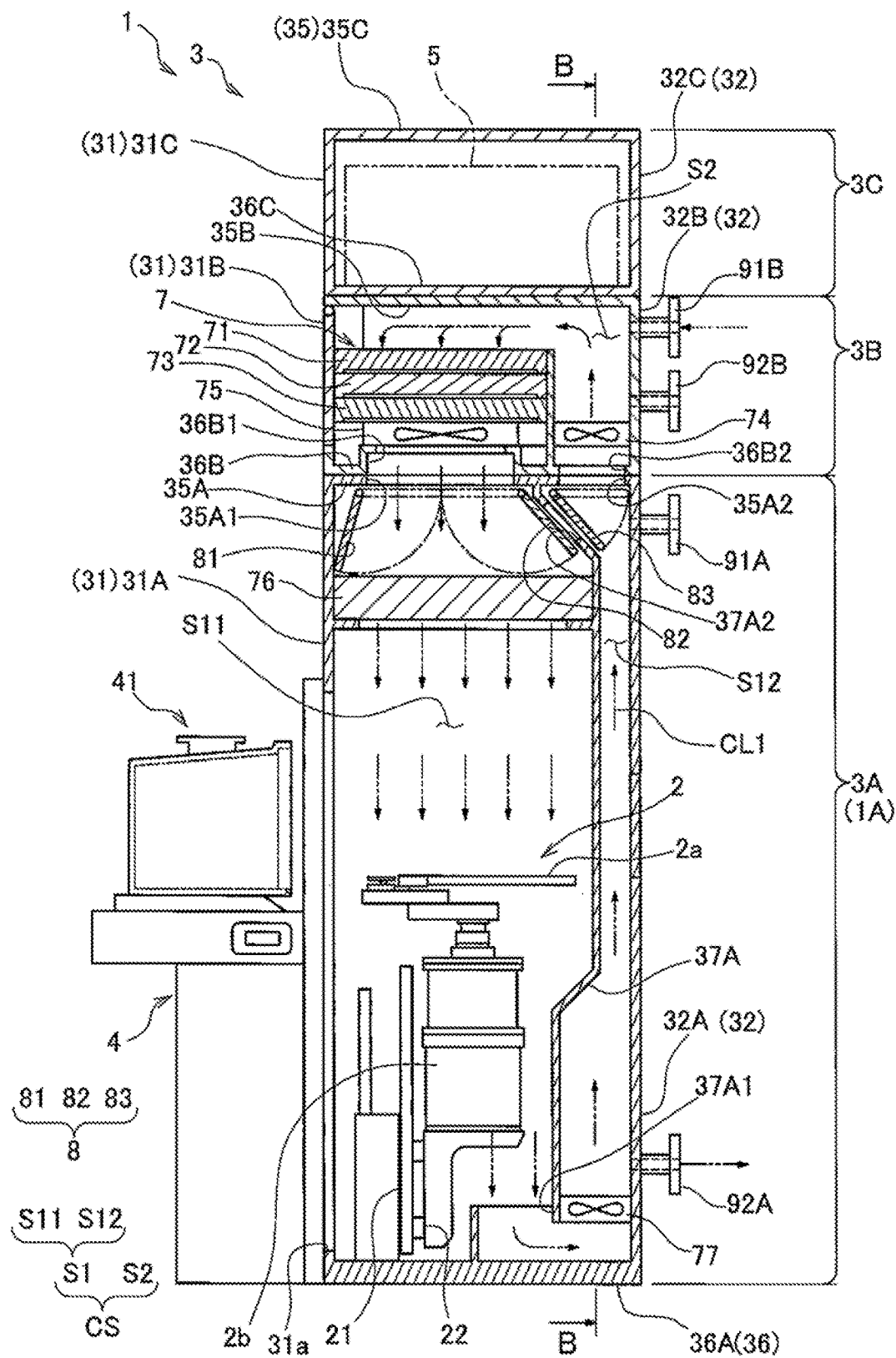
FIG. 3 is a cross-sectional view of the transfer chamber along line A-A of FIG. 1.

FIG. 2 is a perspective view of the transfer chamber 1 seen from the load ports 4 side, and FIG. 3 illustrates a cross-section of the transfer chamber 1 along line A-A of FIG. 1.

As illustrated in FIGS. 2 and 3, the housing 3 which constitutes the transfer chamber 1 includes a main body box 3A, a chemical filter box 3B as a gas processing box, and a control box 3C. The main body box 3A constitutes a transfer chamber main body 1A together with the internal transfer robot 2 (see FIG. 1) and the load ports 4 provided on the front wall 31. The main body box 3A, the chemical filter box 3B, and the control box 3C are mutually separatable.

The front wall 31 of the housing 3 is constituted by front walls 31A, 31B, and 31C, the rear wall 32 is constituted by rear walls 32A, 32B, and 32C, the left side wall 33 is constituted by the left side walls 33A, 33B, and 33C, and the right side wall 34 is constituted by the right side walls 34A, 34B, and 34C of the main body box 3A, the chemical filter box 3B, and the control box 3C, respectively. An upper wall 35 of the housing 3 is constituted by an upper wall 35C of the control box 3C, and a bottom wall 36 of the housing 3 is constituted by a bottom wall 36A of the main body box 3A. A bottom wall 36B of the chemical filter box 3B is in contact with and fixed to the upper wall 35A of the main body box 3A, and a bottom wall 36C of the control box 3C is in contact with and fixed to the upper wall 35B of the chemical filter box 3B.

The load ports 4 are connected to an opening 31a provided in the front wall 31A of the main body box 3A, and a rectangular opening 32a (see FIG. 1) provided in the rear wall 32A is closed with the door 1a which is generally referred to as a gate valve. Two openings 35A1 and 35A2 are provided in the upper wall 35A of the main body box 3A, and openings 36B1 and 36B2 are provided in the bottom wall 36B of the chemical filter box 3B at positions corresponding to the openings 35A1 and 35A2. Therefore, a space S1 in the main body box 3A and a space S2 in the chemical filter box 3B communicate with each other to form a single substantially closed space CS.

The transfer robot 2 provided in the space S1 in the main body box 3A is constituted by an arm portion 2a provided with a pick on which the wafer W is placed and by which the wafer W is transferred, and a base portion 2b which supports the arm portion 2a from below and has a driving mechanism and an ascending/descending mechanism for moving the arm portion 2a. The base portion 2b is supported by the front wall 31A of the main body box 3A via a support portion 21 and a guide rail 22. The transfer robot 2 can move along the guide rail 22 which extends in the width direction in the main body box 3A. When a later-described control means 5 controls an operation of the transfer robot 2, the wafer W contained in a FOUP 41 placed on each of the load ports 4 can be transferred to the load lock chamber 61, and the wafer W after processing in each of the processing units 63 can be again transferred to the FOUP 41.

In the chemical filter box 3B, a chemical filter unit 7 which functions as a gas processing device and is generally referred to as a chemical filter is provided. The chemical filter unit 7 includes an organic matter removal filter 71 for removing an organic matter component among chemical components included in gas which passes through the organic matter removal filter 71, an acid removal filter 72 for removing an acid component, and an alkali removal filter 73 for removing an alkali component. The filters 71 to 73 are independently replaceable. The front wall 31B and the right side wall 34B of the chemical filter box 3B (see FIG. 2) are pivotable upward about an axis provided in an upper part, and by opening these walls, the internal space S2 is opened and the filters 71 to 73 can be replaced. The space S2 can be closed again by moving the front wall 31B and the right side wall 34B down to the vertical positions.

The control means 5 which is a control unit controlling the entire transfer chamber main body 1A is provided inside of the control box 3C. The control means 5 is constituted by an ordinary microprocessor provided with a CPU, memory, and an interface, and so forth. Programs necessary for processing are stored in the memory in advance. The CPU sequentially reads out and executes necessary programs to implement desired functions in cooperation with peripheral hardware resources. As described below, the control means 5 controls operations of the transfer robot 2 in the main body box 3A and the load ports 4, opening and closing of the door 1a and doors 4a, and supply of gas into the main body box 3A or the chemical filter box 3B, for example.

As illustrated in FIG. 3, the space S1 in the main body box 3A is divided into a transfer space S11 which is a space in which the transfer robot 2 operates and a gas return space S12 with an inner wall 37A extending from the bottom wall 36A to the upper wall 35A. An opening 37A1 is provided in a lower part of the inner wall 37A, and the transfer space S11 and the gas return space S12 communicate with each other in the lower part through the opening 37A1. Fans 77 are provided in the lower part of the gas return space S12 to continue with the opening 37A1. When the fans 77 are driven, gas in the transfer space S11 is taken into the gas return space S12 and an upward air flow can be formed within the gas return space S12.

Figure 4:
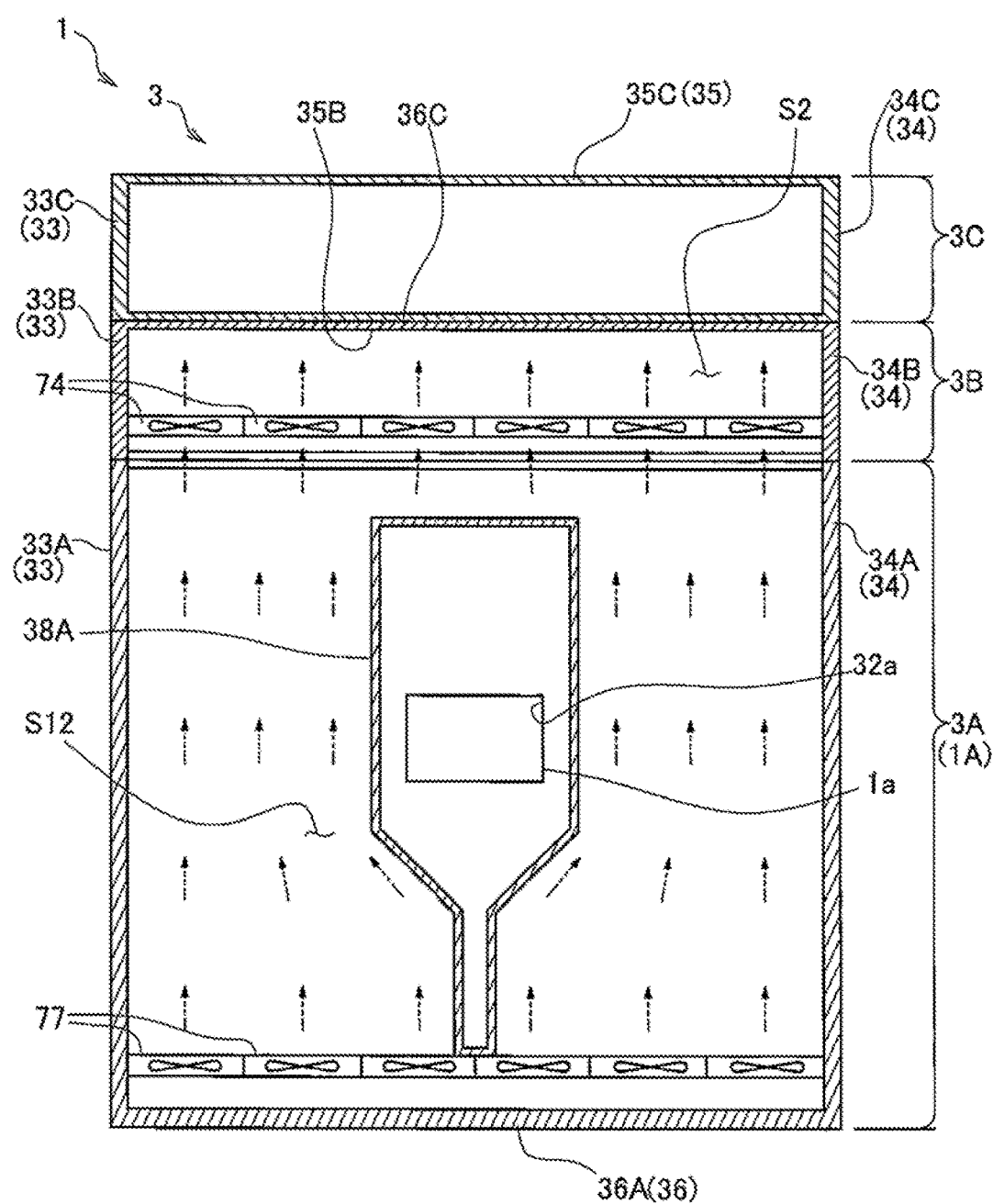
FIG. 4 is a cross-sectional view of the transfer chamber along line B-B of FIG. 3.

FIG. 4 is a cross-sectional view along line B-B of FIG. 3. As illustrated in FIG. 4, a wall portion 38A which surrounds the door 1a to the load lock chamber 61 (see FIG. 1) is formed at the central portion of the gas return space S12, and the space surrounding the door 1a is connected to the transfer space S11 (see FIG. 3). Therefore, the gas return space S12 is divided into two so as to evade the door 1a from below and join again in the upper part.

Returning to FIG. 3, the transfer space S11 and the gas return space S12 communicate with the space S2 in the chemical filter box 3B via the openings 35A1 and 35A2 of the upper wall 35A described above, respectively. Therefore, the transfer space S11 and the gas return space S12 communicate with each other via the space S2 in the chemical filter box 3B also in the upper part.

An FFU 76 is provided in the upper part of the transfer space S11, specifically a position separated slightly from the upper wall 35A. The FFU 76 sends the gas taken in from the space S2 in the chemical filter box 3B out downward so as to form a downward flow in the transfer space S11. A high-performance filter such as a HEPA (High Efficiency Particulate Air) filter and an ULPA (Ultra Low Penetration Air) filter is built in the FFU 76 so that the FFU 76 can collect fine particles contained in the gas passing therethrough.

In the chemical filter box 3B, an exhale fan 75 is provided between the opening 36B1 of the bottom wall 36B described above and the chemical filter unit 7, and an inhale fan 74 is provided above the opening 36B2. The opening 36B2 and the opening 35A2 which continues to the opening 36B2 function as gas inflow ports through which the gas is flown toward the chemical filter unit 7. The inhale fan 74 makes the gas flow into the chemical filter box 3B from the gas return space S12 through the openings 36B2 and 35A2. The opening 36B1 and the opening 35A1 which continues to the opening 36B1 function as gas outflow ports through which the gas is exhausted from the chemical filter unit 7. The exhale fan 75 can send gas which passed the chemical filter unit 7 into the transfer space S11 via the openings 35B1 and 35A1. Therefore, an amount of pressure loss due to the chemical filter unit 7 can be compensated for and a gas flow can be formed with two fans 74 and 75.

As described above, in the substantially closed space CS formed within the main body box 3A and the chemical filter box 3B, the gas which constitutes the internal atmosphere circulates along the following circulation path CL1. That is, the circulation path CL1 is formed to extend downward from the FFU 76 provided in the upper part of the transfer space S11, pass through the opening 37A1 and the fans 77 provided in the lower part of the inner wall 37A, extend upward in the gas return space S12, pass through the openings 35A2 and 36B2, extend into the space S2 in the chemical filter box 3B through the inhale fan 74, pass through the chemical filter unit 7, pass through the exhale fan 75 and the openings 36B1 and 35A1, and return to the transfer space S11. Therefore, it is possible to consider that the chemical filter unit 7 is provided in the midstream of the circulation path CL1.

Thus, in order to supply N2 gas and purge the substantially closed space CS in which the circulation path CL1 is formed, a gas supply port 91A and a gas exhaust port 92A are provided in the rear wall 32A of the main body box 3A, and a gas supply port 91B and a gas exhaust port 92B are provided also in the chemical filter box 3B.

Figure 5:
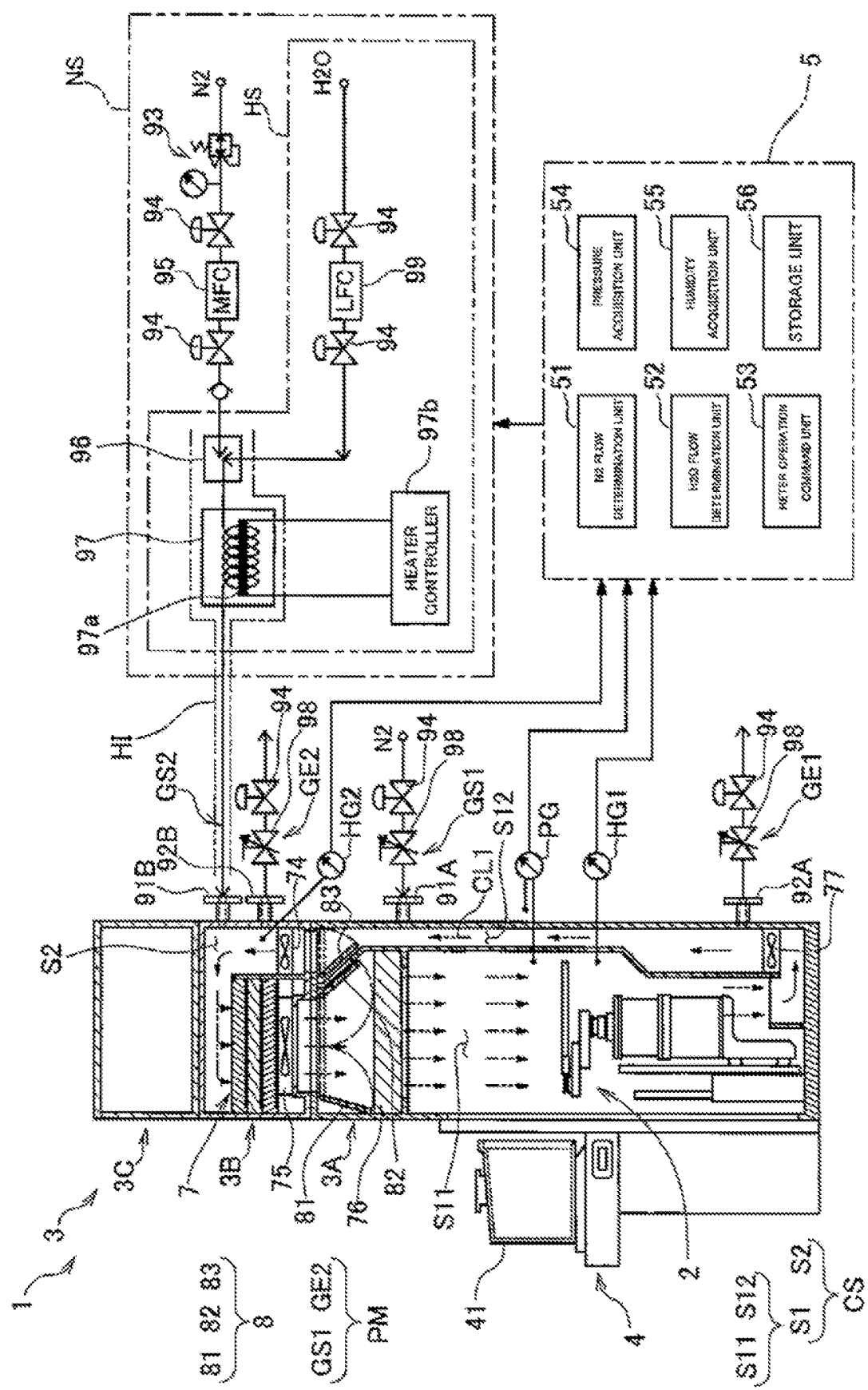
FIG. 5 is a block diagram schematically illustrating a configuration for controlling an internal atmosphere of the transfer chamber.

FIG. 5 schematically illustrates a configuration of the control means 5 which controls the gas exhaust ports 92A and 92B, a piping line connected to the gas supply ports 91A and 91B, and the gas supplied to the piping line. Gas supply lines GS1 and GS2 for guiding N2 gas from an N2 supply source are connected to the gas supply ports 91A and 91B, and gas exhaust lines GE1 and GE2 for guiding N2 gas to N2 exhaust destination are connected to the gas exhaust ports 92A and 92B. Operations of the control means 5 will be described later.

Figure 6:
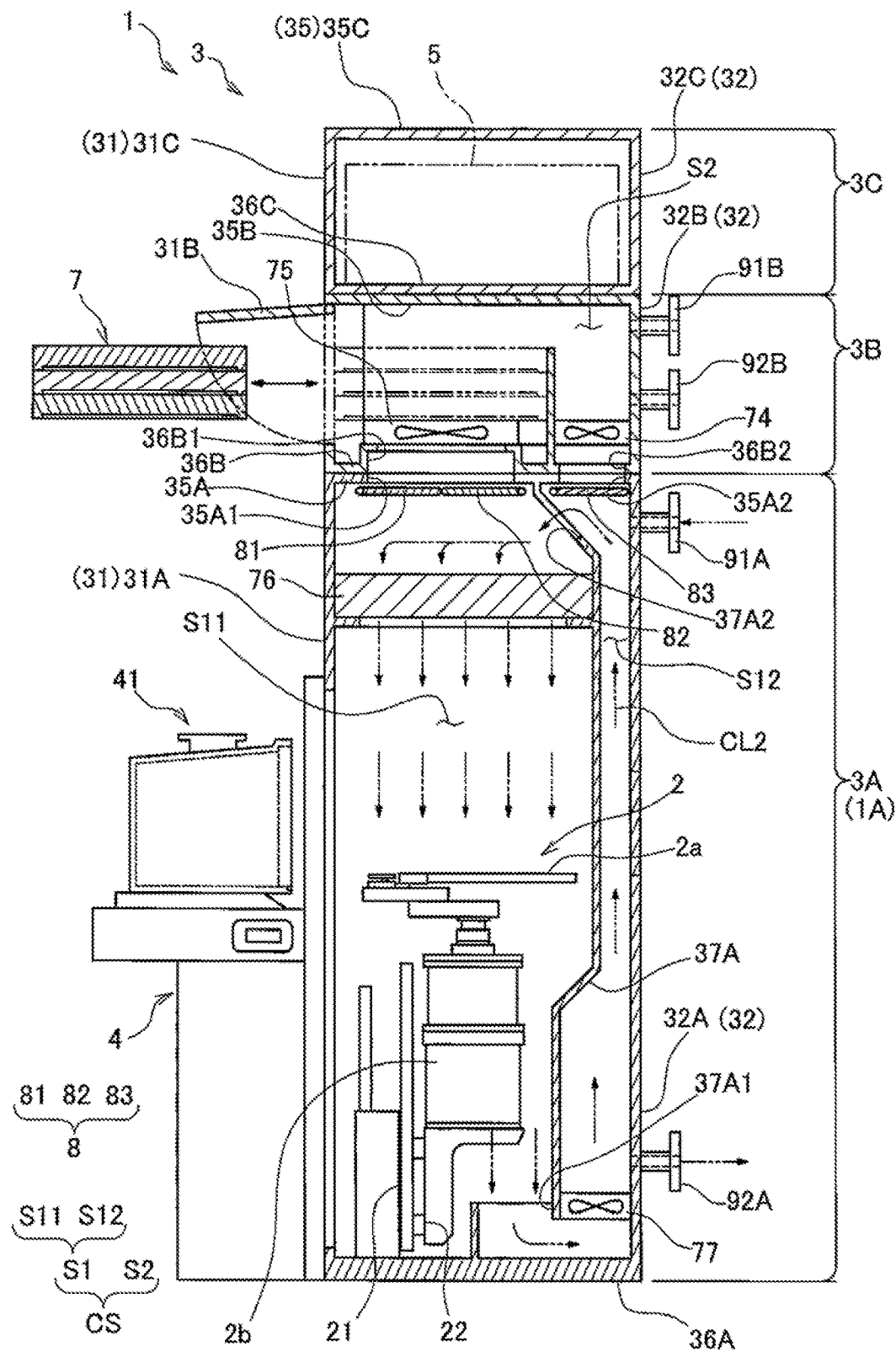
FIG. 6 is a cross-sectional view illustrating a state when removing a chemical filter unit from the transfer chamber.

FIG. 6 illustrates a state in which the substantially closed space CS is divided into the space S1 in the main body box 3A and the space S2 in the chemical filter box 3B, and the front wall 31B of the chemical filter box 3B is opened.

Two dampers 81 and 82 as openable doors are pivotably provided below the above-described opening 35A1. As illustrated in FIG. 3, when the dampers 81 and 82 pivot downward and open so that their ends move apart from each other, the opening 35A1 is opened, and the transfer space S11 and the space S2 in the chemical filter box 3B can communicate with each other through the opening 35A1. Further, as illustrated in FIG. 6, the opening 35A1 can be closed by setting the dampers 81 and 82 to the horizontal position and coming into contact with the inside of the upper wall 35A.

Similarly, a damper 83 as an openable door is pivotably provided below the opening 35A2. As illustrated in FIG. 3, when the damper 83 pivots downward, the opening 35A2 is opened, and the gas return space S12 and the space S2 in the chemical filter box 3B can communicate with each other through the opening 35A2. Further, as illustrated in FIG. 6, the opening 35A2 can be closed by setting the damper 83 to the horizontal position and coming into contact with the inside of the upper wall 35A.

Pivoting of the above-described dampers 81 to 83 may be performed by operating a lever or the like provided in the main body box 3A, or by using a driving mechanism, such as a motor.

An opening 37A2 is provided in an upper part of the inner wall 37A provided in the main body box 3A, and the transfer space S11 and the gas return space S12 can directly communicate with each other through the opening 37A2. However, in an ordinary state in which the dampers 82 and 83 are made to pivot downward so that the openings 35A1 and 35A2 are opened, since these dampers 82 and 83 are in contact with the inner wall 37A to close the opening 37A2, the opening 37A2 is closed in a state in which the openings 35A1 and 35A2 are opened, and no influence is produced in the circulation path CL1 in which the gas flows. On the contrary, in a state in which the openings 35A1 and 35A2 are closed with the dampers 81 to 83, the opening 37A2 is opened. In this case, a new circulation path CL2 as a shortened circulation path which is partially short-circuited in the following manner is formed in the main body box 3A. That is, the new circulation path CL2 is formed to extend downward from the FFU 76 provided in the upper part of the transfer space S11, pass through the opening 37A1 and the fans 77 provided in the lower part of the inner wall 37A, extend upward in the gas return space S12, pass through the opening 37A2 provided in the upper part of the inner wall 37A, and returns to the FFU 76. At this time, the chemical filter unit 7 is disconnected from the circulation path CL1, and the circulation path CL2 is formed by the rest of the parts.

That is, the above-described dampers 81 to 83 function as a disconnecting means 8 for disconnecting the chemical filter unit 7 located in the midstream of the circulation path CL1 from the circulation path CL1, or connecting to the circulation path CL1.

As described above, after disconnecting the chemical filter unit 7 from the circulation path CL1 by the disconnecting means 8, the front wall 31B or the side wall 34B (see FIG. 2) can be opened and the space S2 can be opened, so that the chemical filter unit 7 can be replaced. In this case, since the chemical filter unit 7 is disconnected from the space S1 in the main body box 3A, the space S1 is not exposed to the outside air and can keep a clean state. Therefore, the wafer W can be continuously transferred inside of the transfer chamber main body 1A, while replacing the chemical filter unit 7.

Figure 7:
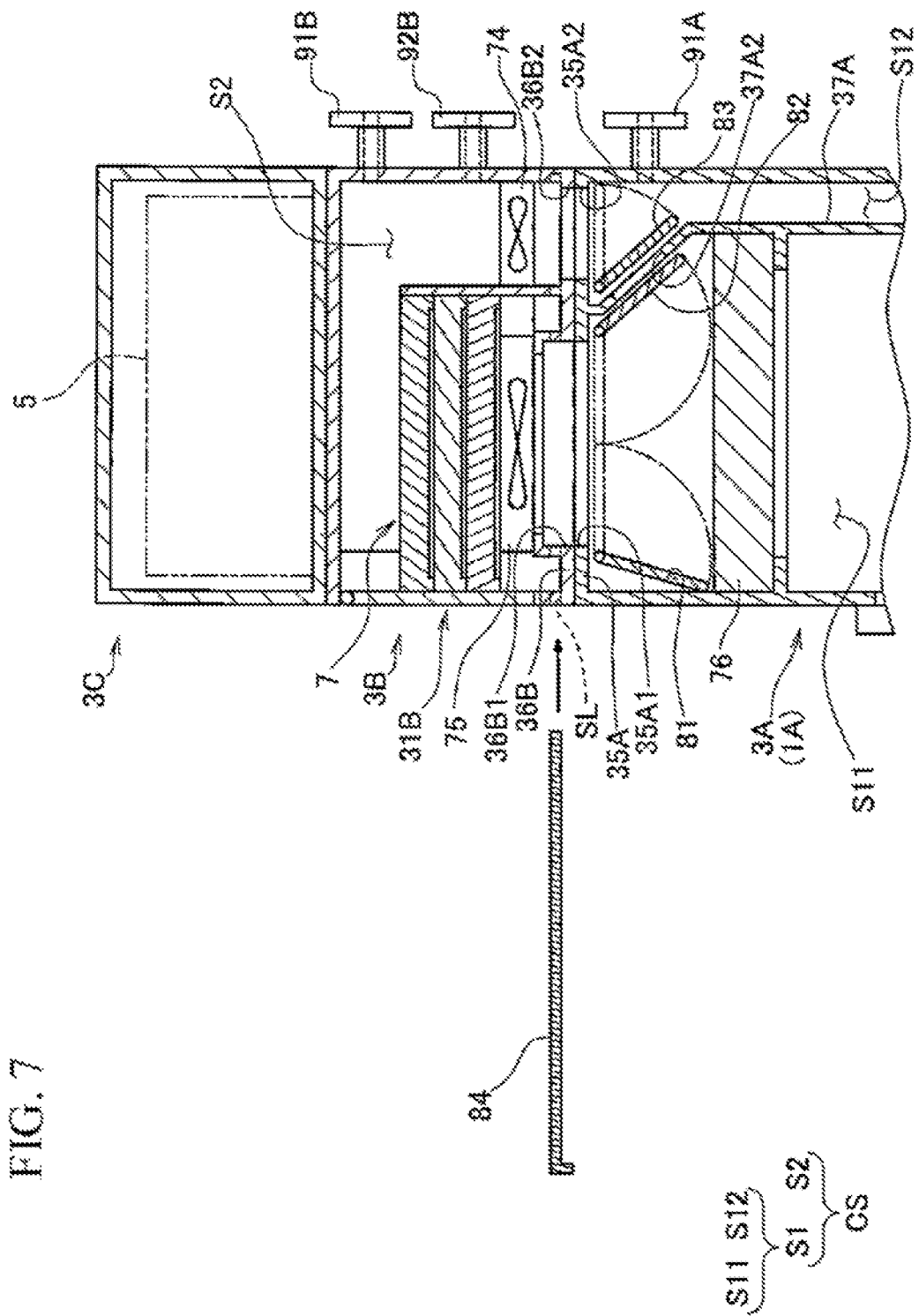
FIG. 7 is an enlarged cross-sectional view illustrating the vicinity of the chemical filter unit of the transfer chamber.

FIG. 7 is an enlarged cross-sectional view of the vicinity of the chemical filter box 3B. In the chemical filter box 3B, a slit SL in which a shield plate 84 can be inserted from the front side is provided. The shield plate 84 is an L-shaped member when seen in a side view formed by a bent sheet metal, is rectangular in shape when seen in a plan view, and slightly smaller than the chemical filter box 3B.

Figure 8A:
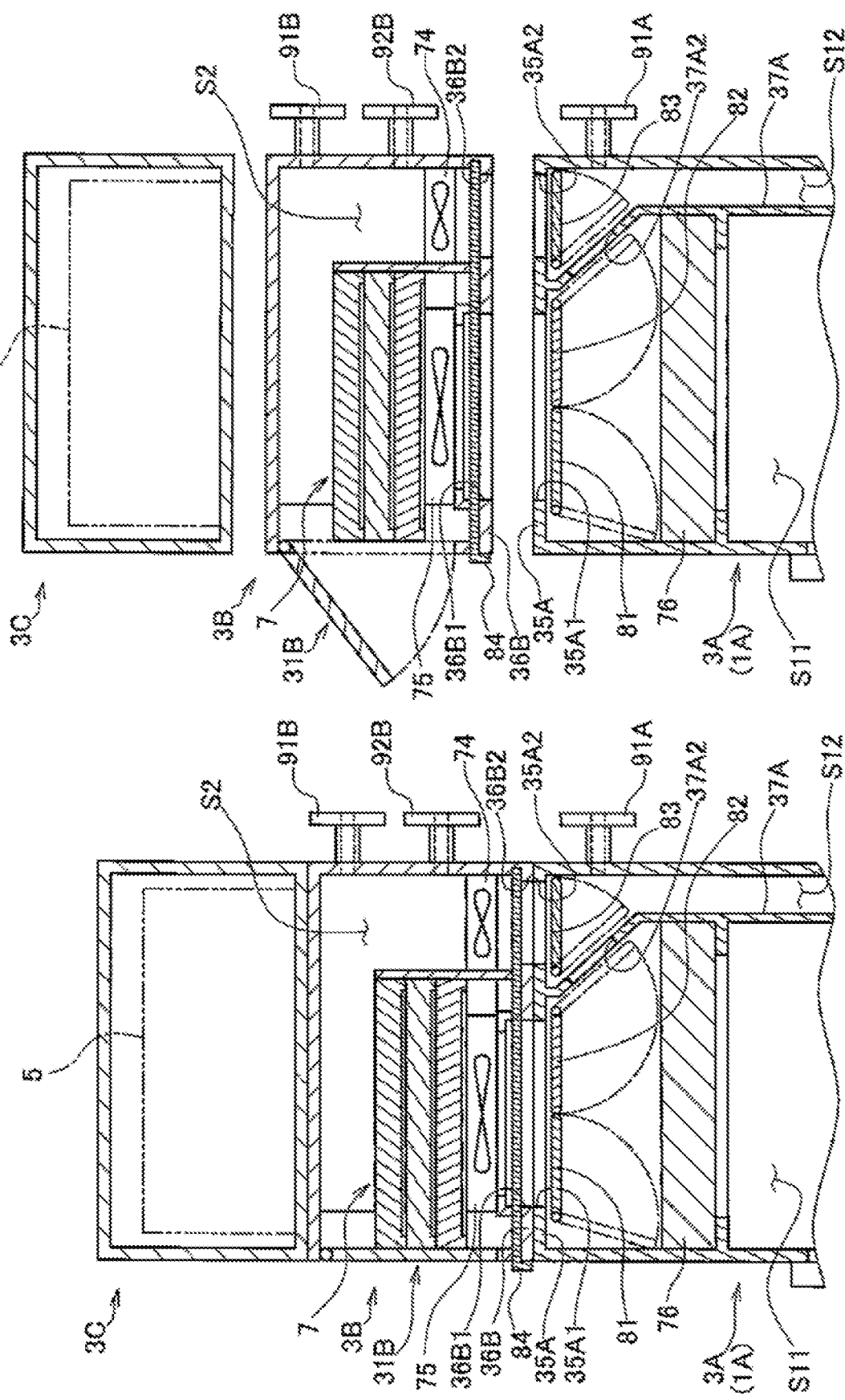
FIG. 8A and FIG. 8B are an explanatory view illustrating a procedure for removing a chemical filter box from the state of FIG. 7.

FIG. 8A illustrates a state in which the shield plate 84 is inserted to a rear direction through the slit SL (see FIG. 7). The shield plate 84 is disposed in parallel to the bottom wall 36B of the chemical filter box 3B, and shields between the openings 36B1, 36 B2, and the internal space S2. Therefore, the space S1 in the main body box 3A and the space S2 in the chemical filter box 3B can be disconnected only by inserting the shield plate 84. The space S2 in the chemical filter box 3B is opened to the outside through the slit SL when the shield plate 84 is extracted. In order to avoid this situation, a dummy plate member may be inserted instead of the shield plate 84 to avoid communication with the outside, and holes may be formed in the dummy plate member at positions corresponding to the openings 36B1 and 36B2 so as not to interfere with the formation of the circulation path CL1 (see FIG. 3).

By inserting the shield plate 84 and closing the above-described dampers 81 to 83, the chemical filter box 3B is disconnected from the circulation path CL1, and a new circulation path CL2 in which the circulation path CL1 is short-circuited (see FIG. 6) can be formed.

Figure 8B:
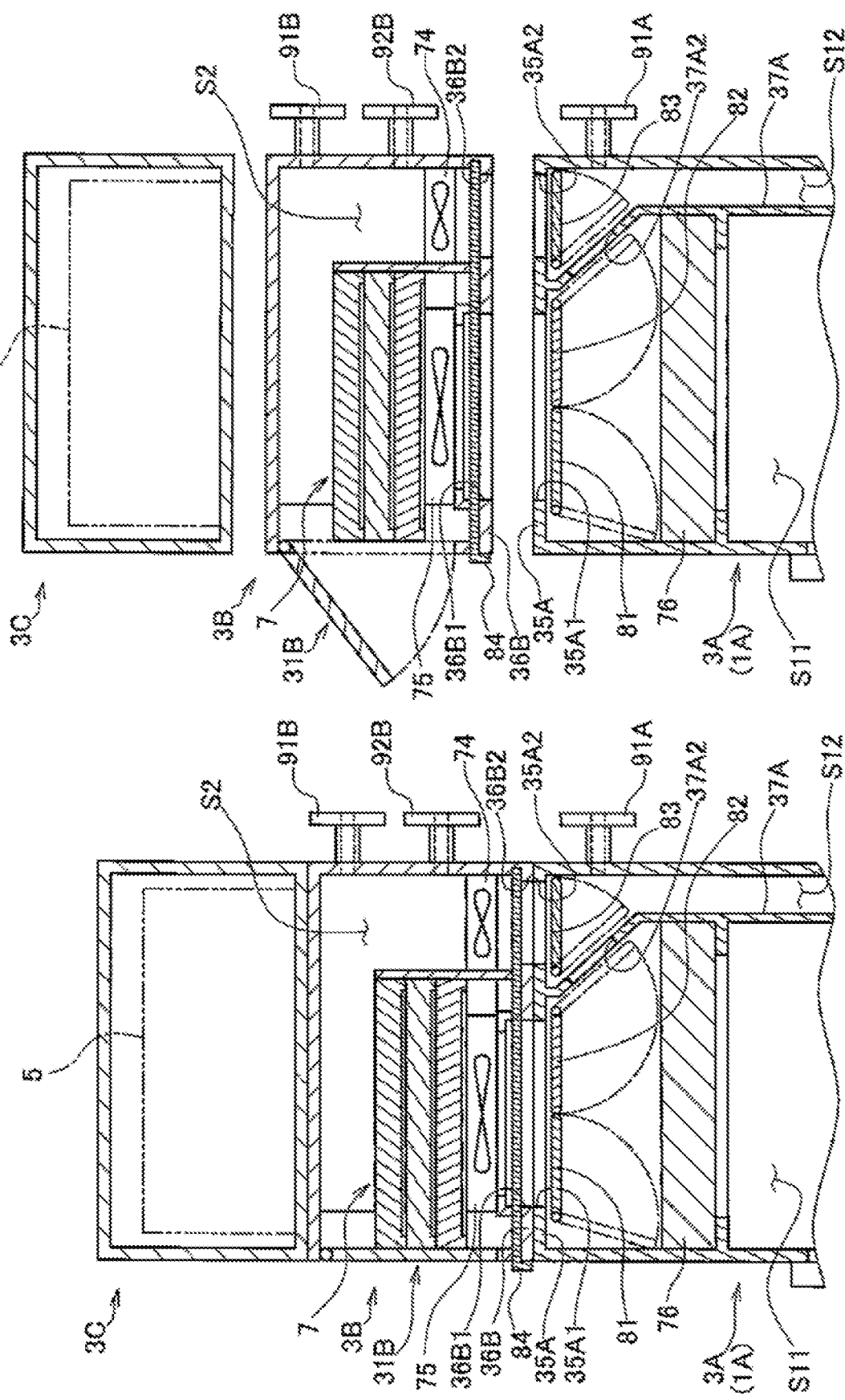

FIG. 8B further illustrates a state in which the chemical filter box 3B and the control box 3C are disconnected from the main body box 3A. Therefore, in a state in which the shield plate 84 is inserted, even if the chemical filter box 3B is disconnected from the main body box 3A and the control box 3C, the chemical filter box 3B can keep the internal space S2 a closed state, and the space S1 in the main body box 3A can be kept in a closed state by the dampers 81 to 83. Therefore, since disconnection can be performed without exposing the inside to the outside air, it is possible to replace the entire chemical filter box 3B, or after moving the chemical filter box 3B to another place, open the front wall 31B or the side wall 34B (see FIG. 2) and replace the chemical filter unit 7. If it is determined from the contents of the process performed to the wafer W that the chemical filter unit 7 is unnecessary, the chemical filter box 3B may be eliminated and the main body box 3A and the control box 3C may be directly connected to each other.

Among the main body box 3A, the chemical filter box 3B, and the control box 3C which constitute the housing 3 as described above, the inside of the main body box 3A and the chemical filter box 3B is purged with N2 gas which is inactive gas to replace the atmosphere so that the surface of the wafer W which is a transferred object is kept clean and occurrence of chemical reactions, such as oxidization, is avoided.

In particular, at the time of initial starting, N2 gas is supplied through the gas supply line GS2 from the gas supply port 91B on the side of the chemical filter box 3B illustrated in FIG. 5, and the internal air is exhausted through the gas exhaust line GE1 from the gas exhaust port 92A.

In the gas supply line GS2, a regulator 93, a valve 94, an MFC (gas flow controller) 95, and the valve 94 are provided in this order in a pipe guided from an N2 gas supply source, and the gas supply line GS2 is connected to the gas supply port 91B. In the gas exhaust line GE1, a flow control valve 98 and the valve 94 are provided in this order in a pipe connected to the gas exhaust port 92A, and an exhaust destination of the gas is connected to an end of the pipe. Therefore, by controlling the supply amount of N2 gas from the gas supply port 91B while controlling the exhaust amount from the gas exhaust port 92A, it is possible to purge air from the space S1 in the main body box 3A and the space S2 in the chemical filter box 3B by filling with N2 gas.

When the density of N2 gas is increased to a certain threshold or higher, the exhaust amount from the gas exhaust port 92A is reduced to a small amount while reducing the supply amount of N2 gas from the gas supply port 91B so as to keep the inside pressure positive. By making the internal gas circulate along the circulation path CL1 in this state, it is possible to remove particles and chemical components contained in the gas by using the FFU 76 and the chemical filter unit 7 and to keep the inside clean. Since N2 gas is dry gas which contains substantially no moisture content, it is possible to reduce the internal moisture content and prevent corrosion on the surface of the wafer W.

Further, in the present embodiment, N2 gas can be supplied to the main body box 3A through the gas supply line GS1, and the gas can be exhausted from the chemical filter box 3B through the gas exhaust line GE2. In the gas supply line GS1, the valve 94, and the flow control valve 98 are provided in this order in a pipe guided from the N2 gas supply source and are connected to the gas supply line GS1. In the gas exhaust line GE2, a flow control valve 98 and the valve 94 are provided in this order in a pipe connected to the gas exhaust port 92B, and an exhaust destination of the gas is connected to an end of the pipe.

Therefore, if the dampers 81 to 83 are closed and the space S1 in the main body box 3A and the space S2 in the chemical filter box 3B are disconnected and are independent from each other, in the main body box 3A, the gas can be exhausted by using the gas supply line GS1 and the gas exhaust line GE1 while slightly supplying fresh N2 gas to the inside. Further, in the chemical filter box 3B, fresh N2 gas can be supplied and the internal gas can be exhausted by using the gas supply line GS2 and the gas exhaust line GE2, and the inside can be purged with N2 gas after the replacement of the chemical filter unit 7. That is, the gas supply line GS2 and the gas exhaust line GE2 constitute a gas purge means PM for performing gas purge of the inside of the chemical filter box 3B. Therefore, even if the chemical filter unit 7 is to be replaced, it is sufficient to replace the small space S2 in the chemical filter box 3B with N2 gas, which reduces consumption of N2.

There is a case that removal performance of chemical components by the chemical filter unit 7 is lowered due to excessively reduced internal moisture content caused by the continued supply of N2 gas used for the replacement of the internal atmosphere as described above.

Among the organic matter removal filter 71, the acid removal filter 72, and the alkali removal filter 73 which constitute the chemical filter unit 7 as illustrated in FIG. 3, the organic matter removal filter 71 removes organic matter components by suction, whereas the acid removal filter 72 and the alkali removal filter 73 remove acid components and alkali components, respectively, by a hydrolysis reaction. Therefore, a certain or greater amount of moisture content is necessary for the removal of acid components or alkali components, and the removal performance is significantly lowered when humidity in the gas becomes excessively lower.

Then, in the present embodiment, in order to keep the internal humidity constant, the following moisture supply means HS is provided so that moisture content can be contained in N2 gas supplied from the gas supply port 91B.

The moisture supply means HS includes the valve 94 connected to a pipe connected to a water supply source, an LFC (Liquid Flow Controller) 99, the valve 94, a sprayer 96 generally called injection, a vaporizer 97, and a heater controller 97b which operates a heater 97a included in the vaporizer 97.

Specifically, the valve 94, the LFC 99, and the valve 94 are connected in this order to the pipe connected to the water supply source, and the pipe is connected to the sprayer 96 provided in the midstream of the gas supply line GS2. Therefore, the moisture content to be applied can be determined by adjusting the water flow by the LFC 99, and the water can be contained in N2 gas as a fine spray of droplets through the sprayer 96. The vaporizer 97 constituted by a pipe formed in a coiled shape and the heater 97a for heating the pipe is provided downstream of the sprayer 96. When power is supplied from the heater controller 97b, the heater 97a can heat the gas flowing through the pipe and can make the water droplets contained in the gas evaporate. A heat insulation means HI constituted by a heat insulation material and a heat-retaining heater is provided in the pipe at a portion from the sprayer 96 to the gas supply port 91B via the vaporizer 97. The heat insulation means HI prevents condensation of once evaporated moisture content and entrance of waterdrops into the chemical filter box 3B.

The gas supply line GS2 to which the moisture supply means HS is added as described above constitutes a gas supply means NS which supplies N2 gas containing moisture content together with the moisture supply means HS.

In order to control such a gas supply means NS, humidity detectors HG1 and HG2 which detect humidity in the space S1 in the main body box 3A and the space S2 in the chemical filter box 3B, respectively, are provided. Further, a pressure sensor PG which detects a pressure difference between the space S1 in the main body box 3A and the outside is provided.

In order to control the gas supply means NS in accordance with the detected values from these sensors, the above-described control means 5 is constituted as follows.

The control means 5 includes a gas (N2) flow determination unit 51, a water (H2O) flow determination unit 52, a heater operation command unit 53, a pressure acquisition unit 54, a humidity acquisition unit 55, and a storage unit 56.

A pressure target value and a humidity target value which are predetermined values defined in advance are stored in the storage unit 56. The pressure acquisition unit 54 can acquire output of the pressure sensor PG and then output as a pressure detection value. The humidity acquisition unit 55 can acquire output of the humidity detectors HG1 and HG2 and then output as humidity detection values.

The gas flow determination unit 51 is configured to determine the flow of N2 gas supplied from the gas supply line GS2 in accordance with the pressure detection value obtained from the pressure acquisition unit 54, and output a corresponding gas flow command value to the MFC 95. Specifically, if the pressure detection value is in a predetermined range around the pressure target value, the gas flow command value is kept, if the pressure detection value is smaller than the above-described predetermined range, the supply amount of N2 gas is increased, and if the pressure detection value is larger than the above-described predetermined range, the gas flow command value is changed so that the supply amount of N2 gas is reduced.

The water flow determination unit 52 is configured to determine the flow of water supplied from the moisture supply means HS in accordance with the humidity detection value by the humidity detector HG2 obtained via the humidity acquisition unit 55, and output a corresponding water flow command value to the LFC 99. Specifically, if the humidity detection value is in a predetermined range around the humidity target value, the water flow command value is kept, if the humidity detection value is smaller than the above-described predetermined range, the supply amount of water is increased, and if the humidity detection value is larger than the above-described predetermined range, the water flow command value is changed so that the supply amount of water is reduced. If the humidity detection value is larger than the humidity target value, the supply amount of water may be set to zero and only N2 gas may be supplied. Regarding the control of humidity, it is also desirable to control overshooting and hunching using PID control. When the above-described control is performed, the humidity detection value by the humidity detector HG1 is used for monitoring, however, the humidity detection value by the humidity detector HG2 may be used for monitoring and the humidity detection value by the humidity detector HG1 may be used for controlling.

The heater operation command unit 53 is configured to provide the heater controller 97b with a command to operate the heater 97a corresponding to the water flow command value determined by the water flow determination unit 52.

Since the transfer chamber 1 is configured as described above, the following operation can be performed.

First, in starting the operation of the transfer chamber 1, the openings 35A1 and 36B1 and the openings 35A2 and 36B2 which continue between the main body box 3A and the chemical filter box 3B are opened by the dampers 81 to 83 which are the disconnecting means 8 as illustrated in FIG. 3.

Then, the space S1 in the main body box 3A and the space S2 in the chemical filter box 3B are connected and a single closed space CS is formed, and a circulation path CL1 for circulating the gas inside the space CS between the transfer space S11, the gas return space S12, and the space S2 in the chemical filter box 3B is formed.

Air is purged from the internal substantially closed space CS with N2 gas from the gas exhaust port 92A via the gas exhaust line GE1 while supplying N2 gas from the gas supply port 91B via the gas supply line GS2 as illustrated in FIG. 5. At this time, the pressure acquisition unit 54 acquires the pressure detection value from the output obtained from the pressure sensor PG, and in accordance with the pressure detection value, the gas flow determination unit 51 determines the gas flow command value and outputs to the MFC 95. Then, the MFC 95 adjusts the gas flow in accordance with the gas flow command value and the flow of N2 gas supplied to the substantially closed space CS is changed. In this manner, the inside of the substantially closed space CS can be kept to have positive pressure which is higher than the pressure of the outside so that entrance of particles from the outside can be prevented.

Further, the gas can be circulated inside along the circulation path CL1 by the control means 5 causing the FFU 76 and the fans 74, 75, and 77 to operate, and particles and chemical components contained in the gas can be removed with the chemical filter unit 7 and the FFU 76 so that a clean state can be obtained.

Further, the humidity acquisition unit 55 which constitutes the control means 5 acquires a humidity detection value from the output obtained from the humidity detector HG2, and in accordance with the humidity detection value, the water flow determination unit 52 determines a water flow command value, and outputs to the LFC 99. The LFC 99 adjusts the water flow in accordance with the water flow command value, and the moisture content contained in N2 gas supplied to the substantially closed space CS is adjusted. After provided as fine droplets by using the sprayer 96, the moisture content is provided to the chemical filter box 3B in an evaporated state by using the vaporizer 97 disposed downstream. In this manner, very low humidity that does not affect the hydrolysis reaction by the chemical filter unit 7 can be kept in the substantially closed space CS, so that chemical components can be effectively removed and corrosion of the wafer W caused by excessively high humidity can also be prevented.

Since the internal atmosphere becomes clean and stabilized as described above, the wafer W which is the transferred object can be transferred by the control means 5 causing the transfer robot 2, the load ports 4 and each of the doors 1a and 4a illustrated in FIG. 1 to operate.

If replacement of the chemical filter unit 7 becomes necessary, as illustrated in FIG. 6, the dampers 81 to 83 which constitute the disconnecting means 8 are operated to close the opening 35A1 and the opening 35A2, and the opening 37A2 formed in the upper part of the inner wall 37A is opened. In this manner, the space S1 in the main body box 3A and the space S2 in the chemical filter box 3B are disconnected, and the circulation path CL2 short-circuited inside of the main body box 3A can be formed. In this case, since circulation of the gas along the circulation path CL2 by the FFU 76 and the fans 77 is continued and fresh N2 gas is supplied from the gas supply port 91A via the gas supply line GS1 (see FIG. 5) in the main body box 3A, the inside can be kept in the clean state. Therefore, the wafer W can be continuously transferred, while replacing the chemical filter unit 7 and operating only the transfer chamber main body 1A.

In the chemical filter box 3B, since the chemical filter unit 7 is disconnected from the circulation path CL1 (CL2) by the disconnecting means 8, the chemical filter unit 7 can be replaced freely without affecting the transfer chamber main body 1A even if the front wall 31B or the side wall 34B (see FIG. 2) is opened.

After replacing the chemical filter unit 7 and closing the front wall 31B and the side wall 34B (see FIG. 2) to set the internal space S2 to a substantially closed state, the space S2 is purged with N2 gas by exhausting air from the gas exhaust port 92B via the gas exhaust line GE2 while supplying N2 gas from the gas supply port 91B illustrated in FIG. 5 via the gas supply line GS2. Thus, since a part exposed to the outside air is limited to the space S2 in the chemical filter box 3B during replacement of the chemical filter unit 7, consumption of N2 gas when performing gas purge again can be reduced and the working hour can be shortened.

Further, when N2 gas is supplied after replacement of the chemical filter unit 7, the humidity detection value is acquired from the output obtained from the humidity detector HG2, and moisture content is supplied to N2 gas from the moisture supply means HS so that the humidity detection value becomes within a predetermined range around the humidity target value. Therefore, at the time of purging the inside of the chemical filter box 3B with N2 gas, it is possible to put the chemical filter unit 7 into a condition that chemical components can be removed properly.

As described above, after the replacement of the chemical filter unit 7, inside of the space S2 in the chemical filter box 3B is purged with N2 gas, the disconnecting means 8 is made to operate again after performing moisture control so as to make the space S1 in the main body box 3A and the space S2 in the chemical filter box 3B communicate with each other, and the circulation path CL1 is formed between the transfer space S11, the gas return space S12, and the space S2 in the chemical filter box 3B. In this manner, the chemical filter unit 7 is connected to the circulation path CL1. Then, supply of N2 gas from the gas supply line 91A and exhaust of the gas from the gas exhaust port 92B are stopped, and a regular control in which a small amount of N2 gas is exhausted from the gas exhaust line 92A while supplying a small amount of N2 gas from the gas supply line 91B is started.

Therefore, even if the chemical filter unit 7 is replaced, it is possible to shorten or eliminate the stop time of the transfer process required for the replacement, with substantially no influence on the transfer of the wafer W. In the present embodiment, as illustrated in FIGS. 7 and 8, since the shield plate 84 is inserted in the chemical filter box 3B, even if the chemical filter box 3B is disconnected from the main body box 3A, the closed condition of the space S2 in the chemical filter box 3B can be kept. Therefore, replacement can be performed without excessively exposing the inside of the chemical filter box 3B to the outside air, or maintenance can be performed after moving the chemical filter box 3B to another place. If the chemical filter box 3B is unnecessary, the control box 3C may be directly connected to the main body box 3A to configure a transfer chamber 1 with no chemical filter unit 7.

As described above, the transfer chamber 1 in the present embodiment is configured to transfer the wafer W which is the transferred object to or from the processing device 6 by using the transfer robot 2 provided thereinside, and include the circulation path CL1 formed inside of the transfer chamber 1 to circulate the gas, the chemical filter unit 7 as the gas processing device provided in the midstream of the circulation path CL1, and the connecting and disconnecting means 8 which switches connection and disconnection of the chemical filter unit 7 to and from the circulation path CL1.

With this configuration, the chemical filter unit 7 can be replaced without affecting the internal atmosphere by disconnecting the chemical filter unit 7 from the circulation path CL1 by the connecting and disconnecting means 8, so that the internal space S1 can be kept clean. Further, since it becomes unnecessary to expose the entire inside of the transfer chamber 1 to the outside air during replacement of the chemical filter unit 7, it is possible to eliminate or shorten the time for adjusting the atmosphere after the chemical filter unit 7 is reconnected to the circulation path CL1. Therefore, it is possible to eliminate or shorten the stop time of the transfer process of the wafer W associated with the replacement of the chemical filter unit 7.

Further, when the chemical filter unit 7 is disconnected from the circulation path CL1 by the connecting and disconnecting means 8, the shortened circulation path CL2 in which the gas circulates without passing through the chemical filter unit 7 is formed. Therefore, also when the chemical filter unit 7 is disconnected by the connecting and disconnecting means 8, gas can continuously circulate through the inside and the inside can be kept clean.

Further, since the connecting and disconnecting means 8 is constituted by the dampers 81 to 83 as the openable lids which open and close the gas inflow port 36B2 through which the gas flows into the chemical filter unit 7, and the gas outflow port 36B1 through which the gas is exhausted from the chemical filter unit 7, the chemical filter unit 7 can be connected to and disconnected from the circulation path CL1 easily.

The transfer chamber 1 includes the transfer chamber main body 1A in which the transfer robot 2 is provided, and the chemical filter box 3B as the gas processing box which contains the chemical filter unit 7. The chemical filter box 3B can be connected to and disconnected from the transfer chamber main body 1A, and when connected, the circulation path CL1 is formed between the chemical filter box 3B and the transfer chamber main body 1A. Therefore, working efficiency of the replacement of the chemical filter unit 7 is improved, and it is possible to select whether the chemical filter box 3B is necessary depending on the type of the wafer W or the contents of the process.

Since transfer chamber 1 includes the gas purge means PM which replaces the atmosphere in the chemical filter box 3B which contains the chemical filter unit 7 when the chemical filter unit 7 is disconnected from the circulation path CL1 by the connecting and disconnecting means 8, even if the chemical filter unit 7 is exposed to the outside air during replacement, the atmosphere near the chemical filter unit 7 can be properly adjusted before the chemical filter unit 7 is connected to the circulation path CL1 by the connecting and disconnecting means 8, and it is possible to reduce the influence on the transfer of the wafer 7.

In addition, the gas processing device is the chemical filter unit 7, and the transfer chamber 1 includes the moisture supply means HS which causes moisture content to be contained in the gas supplied to the chemical filter box 3B, and the control means 5 which controls the moisture supply means HS depending on the humidity in the chemical filter box 3B. Therefore, it is possible to connect the chemical filter unit 7 to the circulation path CL1 after providing sufficient removal ability by adjusting humidity near the chemical filter unit 7 even after the replacement of the chemical filter unit 7, high removal ability can be exhibited immediately after the replacement, and the stop time can be shortened or eliminated.

Note that the specific configuration of each part is not limited to that of the embodiment described above.

For example, although the dampers 81 to 83 which constitute the disconnecting means 8 are provided in the main body box 3A and the shield plate 84 is attachable to the chemical filter box 3B in the above-described embodiment, the dampers 181, 182, and 185 may be provided in a chemical filter box 103B and the shield plate 184 may be attachable to a main body box 103A as illustrated in FIG. 9A and FIG. 9B. In FIG. 9A and FIG. 9B, the same parts as those of the above-described embodiment are denoted by the same reference numerals, and description thereof is omitted. As illustrated in FIG. 9A, the dampers 181 and 182 are provided in an opening 36B1 of a chemical filter box 103B and the damper 185 is provided in an opening 36B2 of the chemical filter box 103B. Also in the main body box 103A, the damper 83 which selectively closes an opening 35A2 provided in an upper wall 35A and an opening 37A2 provided in an inner wall 37A is provided. By opening the openings 36B1 and 36B2 with the dampers 181, 182, and 185, and by opening the opening 35A2 and closing the opening 37A2 with the damper 83, the main body box 103A and the chemical filter 103B can communicate with each other. Further, as illustrated in FIG. 9B, by closing the openings 36B1 and 36B2 with the dampers 181, 182, and 185, and by closing the opening 35A2 and opening the opening 37A2 with the damper 83, the main body box 103A and the chemical filter 103B can be in a disconnected state and the gas can be circulated only through the inside of the main body box 103A. Further, the opening 35A can be closed by inserting the shield plate 184 in the slit SL formed slightly below the opening 35A. Therefore, even if the chemical filter box 103B is disconnected from the main body box 103A, these boxes can be kept mutually closed.

Further, the configuration of FIG. 9A and FIG. 9B may be further deformed and a fan-with-damper in which the dampers 181, 182, and 185 and fans 74 and 75 are integrated may be employed.

Although N2 gas is used as the gas with which the inside is filled in the above-described embodiment, other gases, such as Ar (argon) gas which is the same inactive gas, may also be used. The gas may be changed depending on the contents of the process to the wafer W which is the transferred object.

Not only the chemical filter unit 7 but also a sterilization filter and a particle removal filter may be used as the gas processing device, and these filters may remove or weaken specific components from the circulating gas. In these cases, the same effects as those described above can be provided.

Although the above-described embodiment is constituted as the transfer chamber 1 in which the wafer W used for manufacturing semiconductors is a transferred object, the configuration may be used in the cell culture related field described in Patent Literature 2. That is, the above-described embodiment may also be constituted as a transfer chamber for transferring a culture vessel, such as a petri dish, as a transferred object in a clean closed space. Also in this case, the same effects as those described above can be provided.

If the above-described embodiment is constituted as a transfer chamber in the cell culture related field, sterilization gas, such as hydrogen peroxide, may be used as the gas to circulate inside of the transfer chamber. In that case, a detoxication apparatus for circulating sterilization gas for only a predetermined period and detoxicating sterilization gas after a sterilization purpose is achieved may be used together with or in place of the above-described chemical filter unit 7 as the gas processing device. By containing such a gas processing device in the gas processing box 3B in the same manner as in the above-described embodiment, the same effects as those described above can be provided. An example of the detoxication apparatus may be a decomposition apparatus including a catalyst which decomposes hydrogen peroxide into water and oxygen.

Various changes may be made to other configurations without departing from the scope and spirit of the present invention.

DESCRIPTION OF REFERENCE NUMERALS 1 transfer chamber
1A transfer chamber main body
2 transfer robot
3B chemical filter box (gas processing box)
5 control means
6 processing device
7 chemical filter unit (chemical filter, gas processing device)
8 disconnecting means
36B1 opening (gas outflow port)
36B2 opening (gas inflow port)
81 to 83 damper (openable lid)
CL1 circulation path
CL2 circulation path (shortened circulation path)
HS moisture supply means
PM gas purge means
W wafer (transferred object)

The invention claimed is:

1. A transfer chamber for transferring a transferred object to or from a processing device by using a transfer robot disposed in a transfer space inside of a housing, comprising:
    a circulation path formed in a closed loop inside the transfer chamber so as to circulate gas between the transfer space and a gas return space divided by an inner wall of the transfer chamber;
    a filter or filter device provided in a midstream of the circulation path; and
    a plurality of fans provided in the circulation path, the fans including a fan forming a downward air flow in the transfer space and a fan forming an upward air flow in the gas return space,
    wherein the circulation path includes an opening which is arranged at a position lower than a height where the transfer robot transfers the transferred object, and through which the gas flows out from the transfer space and flows into the gas return space, wherein the circulation path is entirely within the housing,
    the inner wall is provided between a pair of horizontally opposed walls of the housing, the fan forming the upward air flow is provided between one of the pair of horizontally opposed walls and the inner wall,
    the inside of the housing is filled with N2 gas to purge air from the inside of the housing, no air is taken in from an outside of the housing into the inside of the housing when the inside of the housing is controlled to be under the inert gas atmosphere, and the inside of the housing is kept at a positive pressure by N2 gas.

2. The transfer chamber according to claim 1, wherein the gas return space has a plurality of gas return spaces and the gas which flows in the gas return spaces join before a gas processing box which contains the filter or filter device.

3. The transfer chamber according to claim 1, comprising
a gas supply line which supplies N2 gas to the circulation path,
a gas exhaust line which exhausts gas from the circulation path, and
a controller which controls the gas supply line and the gas exhaust line so as to keep the inside pressure positive, and controls the plurality of fans so as to compensate an amount of pressure loss and form a gas flow in the circulation path.

4. The transfer chamber according to claim 1, wherein there are a plurality of gas supply lines and a plurality of gas exhaust lines, each of which is connected to a plurality of portions of the circulation path.

5. The transfer chamber according to claim 1, comprising the transfer robot which is provided in the housing and transfers a transferred object, a load port having a door in connection with the housing, and a controller which controls the transfer robot and the door, wherein the transfer robot operates under the environment of the downward air flow formed in the transfer space.

6. The transfer chamber according to claim 1, comprising a downflow forming fan that forms a downflow in the transport space above the transport space, and an inhale fan making a gas flow into the filter or filter device from the gas return space.

7. The transfer chamber according to claim 6, wherein the inhale fan is provided on the downstream side of the gas return space.

8. The transfer chamber according to claim 6, wherein a plurality of inhale fans are arranged in a direction intersecting with a gas flow in the gas return space.

9. The transfer chamber according to claim 1, wherein an entire space in the filter or filter device is one continuous space.

10. A transfer chamber, filled with an inactive gas, for transferring a transferred object to or from a processing device by using a transfer robot disposed in a transfer space inside of a housing, comprising:
a main body box in which the transfer robot is arranged;
a gas processing box which contains a filter device;
a gas return space for returning the inactive gas to the gas processing box from the main body box; and
an inner wall for dividing a space in the main body box into a transfer space in which the transfer robot operates and the gas return space,
wherein the transfer chamber includes a gas circulation path to extend downward in the transfer space in which the transfer robot operates, extend upward in the gas return space, enter into a space in the gas processing box, pass through the filter device and return to the transfer space,
wherein a plurality of fans are provided in the circulation path, the fans including a fan forming a downward air flow in the transfer space and a fan forming an upward air flow in the gas return space,
wherein the circulation path is entirely within the housing, wherein the transfer space has an inlet port which sucks gas from the transfer space and flows gas into the gas return space, and the inlet port is arranged below a transfer arm of the transfer robot,
wherein the inner wall is provided between a pair of horizontally opposed walls of the housing, and
wherein the fan forming the upward air flow is provided between one of the pair of horizontally opposed walls and the inner wall,
the inside of the housing is filled with N2 gas to purge air from the inside of the housing, no air is taken in from an outside of the housing into the inside of the housing when the inside of the housing is controlled to be under the inert gas atmosphere, and the inside of the housing is kept at a positive pressure by N2 gas.

11. The transfer chamber according to claim 10, wherein the gas return space has a plurality of gas return spaces and the gas which flows in the gas return spaces join before the gas processing box.

12. The transfer chamber according to claim 10, comprising
a gas supply line which supplies N2 gas to the circulation path,
a gas exhaust line which exhausts gas from the circulation path, and
a controller which controls the gas supply line and the gas exhaust line so as to keep the inside pressure positive, and controls the plurality of fans so as to compensate an amount of pressure loss and form a gas flow in the circulation path.

13. The transfer chamber according to claim 10, wherein there are a plurality of gas supply lines and a plurality of gas exhaust lines, each of which is connected to a plurality of portions of the circulation path.

14. The transfer chamber according to claim 10, comprising the transfer robot which is provided in the housing and transfers a transferred object, a load port having a door in connection with the housing, and a controller which controls the transfer robot and the door, wherein the transfer robot operates under the environment of the downward air flow formed in the transfer space.

15. The transfer chamber according to claim 10, comprising a plurality of inhale fans provided on the downstream side of the gas return space, the plurality of inhale fans make a gas flow into the gas processing box from the gas return space, and the plurality of inhale fans are arranged in a direction intersecting the gas flow in the gas return space.

16. The transfer chamber according to claim 10, wherein an entire space in the gas processing box is one continuous space.

17. A transfer chamber for transferring a transferred object to or from a processing device by using a transfer robot disposed in a transfer space inside of a housing, comprising:
a circulation path formed in a closed loop inside the transfer chamber so as to circulate gas between the transfer space and a gas return space divided by an inner wall of the transfer chamber;
a filter or a filter device provided in a midstream of the circulation path; and
a plurality of fans provided in the circulation path, the fans including a fan forming a downward air flow in the transfer space and a fan forming an upward air flow in the gas return space,
wherein the circulation path includes an opening which is arranged at a position lower than a height where the transfer robot transfers the transferred object, and through which the gas flows out from the transfer space and flows into the gas return space, wherein the circulation path is entirely within the housing,
the inside of the housing is filled with N2 gas to purge air from the inside of the housing, no air is taken in from an outside of the housing into the inside of the housing when the inside of the housing is controlled to be under the inert gas atmosphere, and the inside of the housing is kept at a positive pressure by N2 gas.

18. The transfer chamber according to claim 17, wherein the gas return space has a plurality of gas return spaces and the gas which flows in the gas return spaces join before a gas processing box which contains the filter or filter device.

19. The transfer chamber according to claim 17, wherein an entire space in the filter or filter device is one continuous space.

20. The transfer chamber according to claim 17, comprising a controller which controls the plurality of fans so as to compensate an amount of pressure loss and form a gas flow in the circulation path.

* * * * *